(12) United States Patent
Kobuß et al.

(10) Patent No.: US 7,971,298 B2
(45) Date of Patent: Jul. 5, 2011

(54) UPHOLSTERY ELEMENT FOR A PATIENT BED OF AN OPERATING TABLE

(75) Inventors: Matthias Kobuß, Gaggenau (DE); Jan Donat Olszewski, Rastatt (DE); Bernhard Katzenstein, Baden-Baden (DE)

(73) Assignee: Maquet GmbH & Co. KG., Rastatt (DE)

(*) Notice: Subject to any disclaimer, the term of this patent is extended or adjusted under 35 U.S.C. 154(b) by 311 days.

(21) Appl. No.: 11/595,011

(22) Filed: Nov. 9, 2006

(65) Prior Publication Data

US 2007/0101499 A1    May 10, 2007

(30) Foreign Application Priority Data

Nov. 10, 2005  (DE) .................. 10 2005 053 755

(51) Int. Cl.
A47B 97/00    (2006.01)
(52) U.S. Cl. ................................. 5/621; 5/630
(58) Field of Classification Search .............. 5/691, 722, 5/723, 727, 621, 630
See application file for complete search history.

(56) References Cited

U.S. PATENT DOCUMENTS

| | | | | |
|---|---|---|---|---|
| 1,375,061 A | * | 4/1921 | Nyhus | 5/716 |
| 3,328,079 A | | 6/1967 | Byczkowski et al. | |
| 3,982,741 A | * | 9/1976 | Mitchell et al. | 5/614 |
| 5,083,331 A | | 1/1992 | Schnelle et al. | |
| 5,272,779 A | * | 12/1993 | Payton | 5/698 |
| 5,396,672 A | | 3/1995 | Brown | |
| 5,400,448 A | * | 3/1995 | Zwickey | 5/691 |
| 5,477,570 A | | 12/1995 | Hannant et al. | |
| 5,611,638 A | | 3/1997 | Dorr et al. | |
| 5,621,932 A | | 4/1997 | Strachan | |
| 5,651,150 A | | 7/1997 | Kanitzer et al. | |
| 5,754,997 A | | 5/1998 | Lussi et al. | |
| 5,953,779 A | * | 9/1999 | Schwartz | 5/722 |
| 6,163,909 A | * | 12/2000 | Lin | 5/713 |
| 6,351,678 B1 | | 2/2002 | Borders | |
| 6,421,854 B1 | * | 7/2002 | Heimbrock | 5/610 |
| 6,493,417 B1 | | 12/2002 | Baer et al. | |

(Continued)

FOREIGN PATENT DOCUMENTS

DE    296 10 726 U1    9/1996

(Continued)

OTHER PUBLICATIONS

European Search Report for Serial No. EP 06 12 3598 dated Feb. 8, 2007.

(Continued)

Primary Examiner — Shane Bomar
Assistant Examiner — Gilbert Y Lee
(74) Attorney, Agent, or Firm — McCormick, Paulding & Huber LLP

(57) ABSTRACT

What is shown is an upholstery element for a bed of an operating table, with a baseplate, two elongate side parts comprising dimensionally stable foam, which are arranged along two mutually opposite edges of the baseplate, and an upholstery part which consists at least partially of soft foam and fits between the elongate side parts such that it bears at least with its outsides at least partially against the respectively adjacent side part, at least one projecting portion being formed and arranged at least on one side part such that the said portion engages into an associated recess on the outside of the upholstery part when the upholstery part is arranged between the side parts.

15 Claims, 3 Drawing Sheets

U.S. PATENT DOCUMENTS

| | | |
|---|---|---|
| 6,598,275 B1 | 7/2003 | Kolody et al. |
| 6,848,138 B1* | 2/2005 | Maier et al. ............ 5/730 |
| 6,901,619 B1* | 6/2005 | Hsia ..................... 5/710 |
| 6,902,320 B2* | 6/2005 | McKenna ............ 378/208 |
| 7,181,791 B2 | 2/2007 | Clayton |
| 7,415,741 B1* | 8/2008 | Wasley et al. ............ 5/621 |
| 2002/0170115 A1 | 11/2002 | Borders et al. |
| 2003/0061660 A1 | 4/2003 | Easterling |
| 2003/0078144 A1 | 4/2003 | Gehrke |
| 2004/0194673 A1 | 10/2004 | Comeaux et al. |
| 2005/0273941 A1* | 12/2005 | Stolpmann et al. ........ 5/727 |
| 2006/0031995 A1* | 2/2006 | Barkhouse .............. 5/690 |
| 2006/0219690 A1* | 10/2006 | Grinstead et al. ....... 219/217 |
| 2007/0107123 A1 | 5/2007 | Koch |
| 2007/0107124 A1 | 5/2007 | Koch |
| 2007/0107125 A1 | 5/2007 | Koch |
| 2007/0107126 A1 | 5/2007 | Koch |
| 2007/0107129 A1 | 5/2007 | Burstner |
| 2007/0110448 A1 | 5/2007 | Ruch |
| 2007/0116512 A1 | 5/2007 | Katzenstein |
| 2007/0118989 A1 | 5/2007 | Koch |

FOREIGN PATENT DOCUMENTS

| | | |
|---|---|---|
| DE | 197 51 320 A1 | 5/1999 |
| DE | 102 53 878 A1 | 5/2004 |
| DE | 102 53 906 A1 | 6/2004 |
| EP | 0 457 246 A1 | 11/1991 |
| EP | 0 913 139 A | 5/1999 |
| FR | 2484248 | 12/1981 |
| GB | 1 321 193 | 6/1973 |
| GB | 2057830 A | 4/1981 |
| GB | 2 277 870 A | 11/1994 |
| SU | 1393421 A1 | 5/1988 |
| WO | 02 055001 A1 | 7/2002 |
| WO | 03 086263 A1 | 10/2003 |

OTHER PUBLICATIONS

European Search Report for Serial No. EP 06 12 3596 dated Sep. 7, 2007.

European Search Report for Serial No. EP 06 12 3592 dated Nov. 29, 2007.

European Search Report for Serial No. EP 06 12 3593 dated Dec. 4, 2007.

European Search Report for Serial No. EP 06 12 3443 dated Feb. 7, 2007.

Frosin V.N. et al, "Krankenhausausrustung" Moscow, Medizina, 1982, p. 19, depiction 3.

European Search Report for Application No. 06 12 3442, dated Sep. 1, 2008.

* cited by examiner

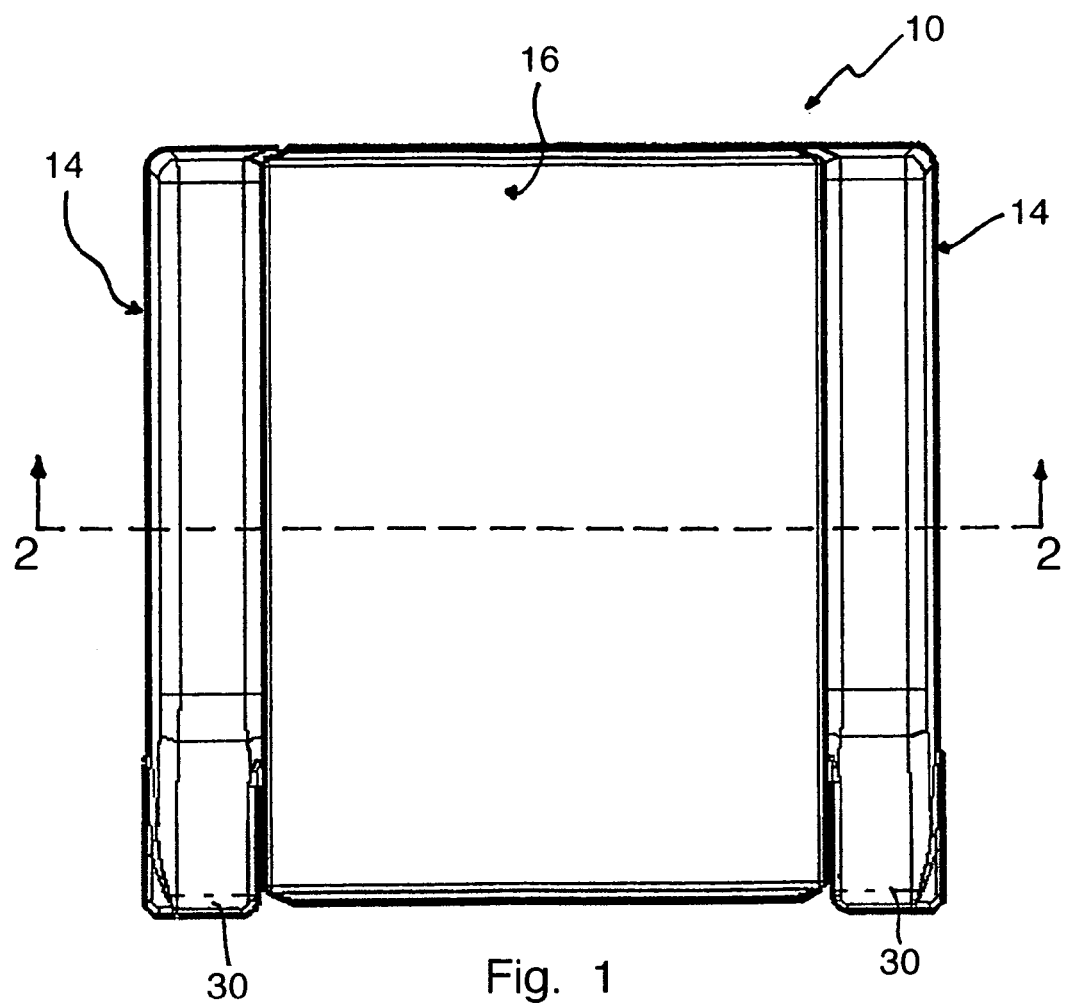
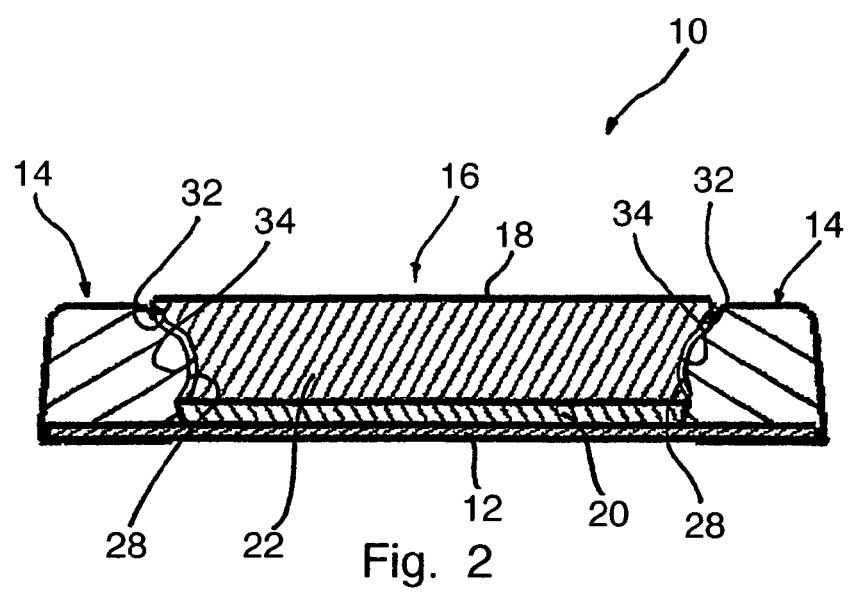

UPHOLSTERY ELEMENT FOR A PATIENT BED OF AN OPERATING TABLE

CROSS REFERENCE TO RELATED APPLICATIONS:

Applicant hereby claims foreign priority benefits under U.S.C. §119 from German Patent Application No. 10 2005 053 755.3 filed on Nov. 10, 2005, the contents of which are incorporated by reference herein.

FIELD OF THE INVENTION

The present invention relates to an upholstery element for a patient bed, for example for a bed of an operating table.

BACKGROUND OF THE INVENTION

Operating tables typically have a bed which comprises a plurality of segments adjustable in relation to one another. Upholstery elements, on which the patient is supported, are fastened to the various segments. Conventionally, the upholstery elements comprise dimensionally stable integral foam, by means of which suitable shapes and structures can easily be produced. Integral foam has the disadvantage, however, that it is relatively hard, and therefore a patient may acquire pressure marks from being supported on an upholstery element of this type for a lengthy period of time.

In principle, in addition to the integral foam upholstery, a softer upholstery may be used, which is fastened to the integral foam upholstery by means of bands or touch-and-close fastenings. However, fastening means of this type, such as straps, bands or touch-and-close connections, cannot easily be cleaned and therefore present a problem in terms of hygiene. Moreover, the fastening and release of additional soft upholsteries are complicated and therefore time-consuming.

SUMMARY OF THE INVENTION

The object on which the invention is based is to specify an upholstery element of the type mentioned in the introduction, which can easily be handled and cleaned and at the same time enables the patient to have a soft support.

This object is achieved by means of an upholstery element comprising a baseplate, two elongate side parts comprising of dimensionally stable foam which are arranged along two mutually opposite edges of the baseplate, and an upholstery part which comprises at least partially of soft foam and fits between the elongate site parts such that it bears at least with its outsides at least partially against the respectively adjacent side part, at least one projecting portion being formed and arranged at least on one side part such that the said portion engages into an associated recess on the outside of the upholstery part when the upholstery part is arranged between the side parts.

In the upholstery element according to the invention, therefore, an upholstery part is provided which comprises at least partially of soft foam and thus enables a patient to have a soft support by means of which pressure points can be avoided. The softer upholstery part acquires a lateral hold due to the dimensionally stable side parts between which it can be placed. At the same time, the upholstery part is retained in this position as a result of the engagement of the at least one projecting portion into its associated recess, without additional fastening means, such as touch-and-close connections, bands or straps, being required. As a result, the upholstery element can be cleaned easily and thoroughly and can be handled in a simple way.

Preferably, the side parts comprise integral foam, in particular PUR (polyurethane) integral foam.

The upholstery part is preferably surrounded by a water-impermeable sheath and can therefore be washed off. It comprises preferably a lower layer of EPDM (ethylene-propylene-terpolymer) and an upper layer of soft foam. The upper layer of soft foam enables the patient to have a soft support. The lower layer comprising the somewhat harder EPDM can engage under the projecting portions of the side parts, with the result that the upholstery part is held more securely during use.

The upholstery part is preferably surrounded by a water-impermeable sheath and can therefore be washed off. It comprises preferably a lower layer of EPDM and an upper layer of soft foam. The upper layer of soft foam enables the patient to have a soft support. The lower layer comprising of the somewhat harder EPDM can engage under the projecting portions of the side parts, with the result that the upholstery part is held more securely during use.

The baseplate preferably comprises a material permeable to X-rays, in particular of plastic, so that the patient, when lying on the operating table, can undergo X-ray examination.

The upholstery element is preferably suitable for being arranged on a segment of a bed of an operating table which is connected in an articulated manner to a further segment of the bed. In this case, a shaped portion is formed on at least one of the longitudinal ends of at least one of the side parts, such that the said shaped portion at least partially covers a joint between the two segments. This prevents a patient who is supported, using the upholstery element, from coming into contact with the joint. Such a shaped portion requires a complex structure since it must allow the various positions of the joint. However, a complex structure of this type can be produced exceedingly well by means of integral foam.

Finally, the invention relates, furthermore, to an operating table with a bed which comprises a plurality of segments adjustable in relation to one another, an upholstery element according to one of the abovementioned developments being arranged on at least one of the segments.

BRIEF DESCRIPTION OF THE DRAWINGS

For a clearer understanding of the present invention, reference is made below to the preferred exemplary embodiment which is illustrated in the drawings and which is described by means of specific terminology. It may be pointed out, however, that the scope of protection of the invention is not to be restricted thereby, since such variations and further modifications to the device shown and such further applications of the invention as are indicated in it are considered as the customary current and future specialized knowledge of a competent person skilled in the art. An exemplary embodiment of the invention is shown in the figures in which, to be precise, FIG. 1 shows a top view of an upholstery element according to an embodiment of the invention, FIG. 2 shows a cross-sectional view along the line 2-2 of FIG. 1.

DETAILED DESCRIPTION OF THE INVENTION

Figure 3:
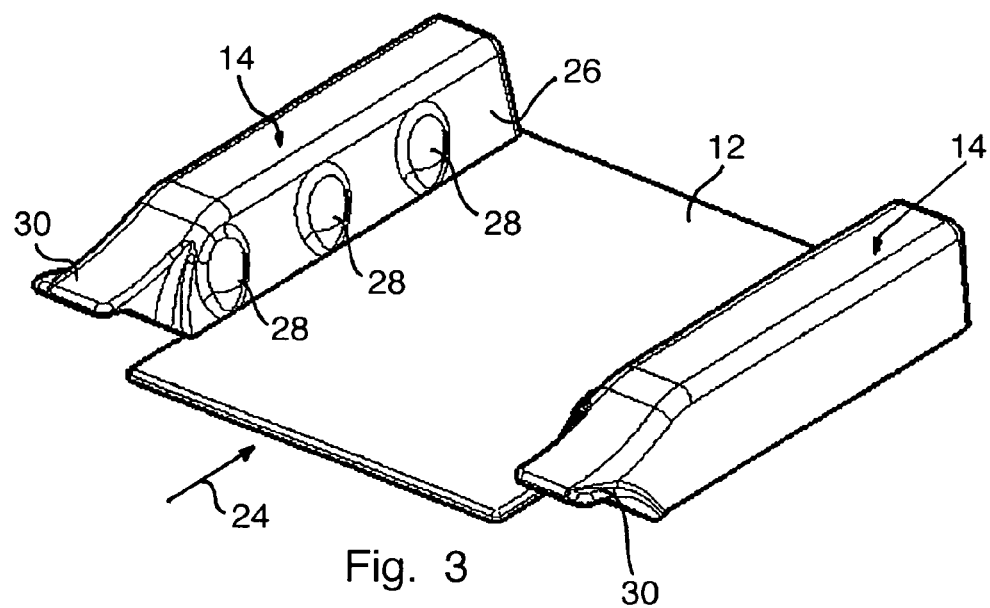
FIG. 3 shows a perspective view of the upholstery element.

FIG. 1 shows a top view of an upholstery element 10 according to an embodiment of the invention, and FIG. 2 shows a cross section through the upholstery element 10 along the line 2-2 of FIG. 1.

The upholstery element 10 is intended to be arranged on a segment of a bed of an operating table (not shown). As shown in FIG. 1 and FIG. 2, the upholstery element 10 comprises a baseplate 12, at the longitudinal edges of which side parts 14 comprising dimensionally stable foam are arranged. In this case, longitudinal edges designate the edges of the baseplate 12 which are arranged in the longitudinal direction of the bed of the operating table when the upholstery element 10 is arranged on the operating table.

The baseplate 12 comprises plastic permeable to X-rays. Radiographs of a patient supported on the upholstery element 10 can therefore be taken through the latter.

The upholstery element 10 further comprises an upholstery part 16 which is arranged, lying on the baseplate 12, between the elongate side parts 14. The upholstery part 16 is surrounded completely by a water-impermeable sheath 18 which can be washed off. It contains a core which comprises a lower layer 20 of ethylene-propylene-terpolymer foam (EPDM foam) and of an upper layer 22 of soft foam. The sheath 18 may be electrically conductive at least on its outer surface.

The upholstery part 16 can be placed onto the baseplate 12 between the side parts 14, as shown in FIGS. 1 and 2, and is held in this position in a way described in more detail below. The upholstery part 16 can be removed from this position, for example for cleaning.

Figure 4:
FIG. 4 shows a front view of the upholstery element of FIGS. 1 and 2 in which the upholstery part has been removed.
Figure 5:
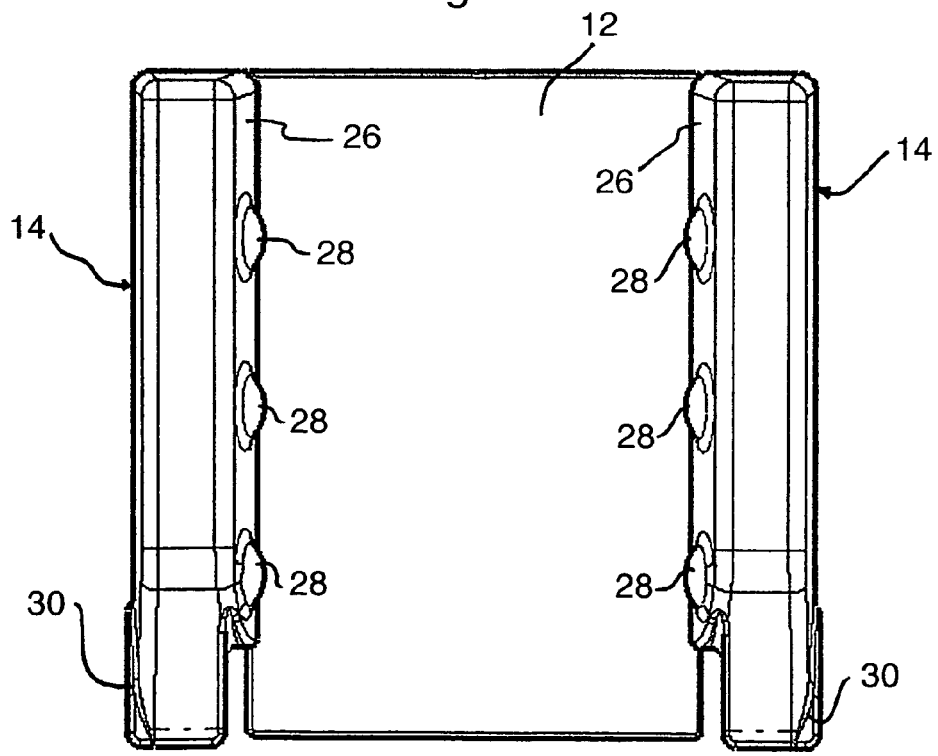
FIG. 5 shows a top view of the upholstery element of FIGS. 1 and 2 in which the upholstery part has been removed.

FIGS. 3 to 5 illustrate the upholstery element 10, with the upholstery part 16 removed. In this case, FIG. 3 shows a perspective view of the baseplate 12 and the two side parts 14. FIG. 4 shows a front view, that is to say a view from the viewing direction of the arrow 24 of FIG. 3, and FIG. 5 shows a top view of the baseplate 12 and the side parts 14.

As already mentioned above, the side parts comprise dimensionally stable foam, from which the structured shape of the side parts 14, which is to be seen in FIGS. 3 to 5, can easily be produced. Preferably, the side parts 14 comprise a structured foam or integral foam with a solid, non-foamed outer skin, for example of PUR (polyurethane) integral foam. As shown in FIGS. 3 to 5, the side parts 14 each have an inwardly directed side 26 on which three projecting bosses 28 are formed in each case. The bosses 28 have a convex, for example part-spherical configuration. The side parts 14 may be lacquered with an electrically conductive lacquer, so that, in conjunction with the electrically conductive sheath 18 of the upholstery part 16, statutory electrical conduction discharge is obtained on the surface of the upholstery element 10.

A shaped portion 30 is formed in each case at one of the longitudinal ends of the side parts 14. The shaped portion 30 is intended for partially covering a joint which is arranged between two adjacent segments (not shown) of the bed of an operating table. This ensures that a patient supported on the bed does not come into contact with the joint. The complex structure of the side parts 14, which is shown in FIGS. 3 to 5, can be produced in a relatively simple way from integral foam.

The bosses 28 are intended for retaining the upholstery element 16 when the latter is arranged, lying on the baseplate 12, between the side parts 14, as shown in FIGS. 1 and 2. In this position, the bosses 28 engage into associated recesses 34 of the upholstery part 16 which are formed on the outside 32 of the upholstery part 16 (see FIG. 2). This prevents the upholstery part 16 from slipping out of place in relation to the baseplate 12 and to the side parts 14. A contribution to this is made, in particular, by the lower layer 20 of the upholstery 16, which comprises EPDM foam and is therefore more rigid than the viscoelastic soft foam of the upper layer 22 and which engages under the bosses 28.

The upholstery element 10 from FIGS. 1 to 5 thus has a middle lying portion which is formed by the soft upholstery part 16 and on which a patient can be supported for a long time, without pressure marks being formed on his body. At the same time, the upholstery element has the more rigid side parts 14, by means of which the upholstery part is retained in its predetermined position and which gives the upholstery part 16 a lateral hold. Furthermore, the side parts 14 have a suitable structure, in order to cover further components of the operating table (not shown), for example longitudinal spars of the segments or joints between the segments.

Figure 6:
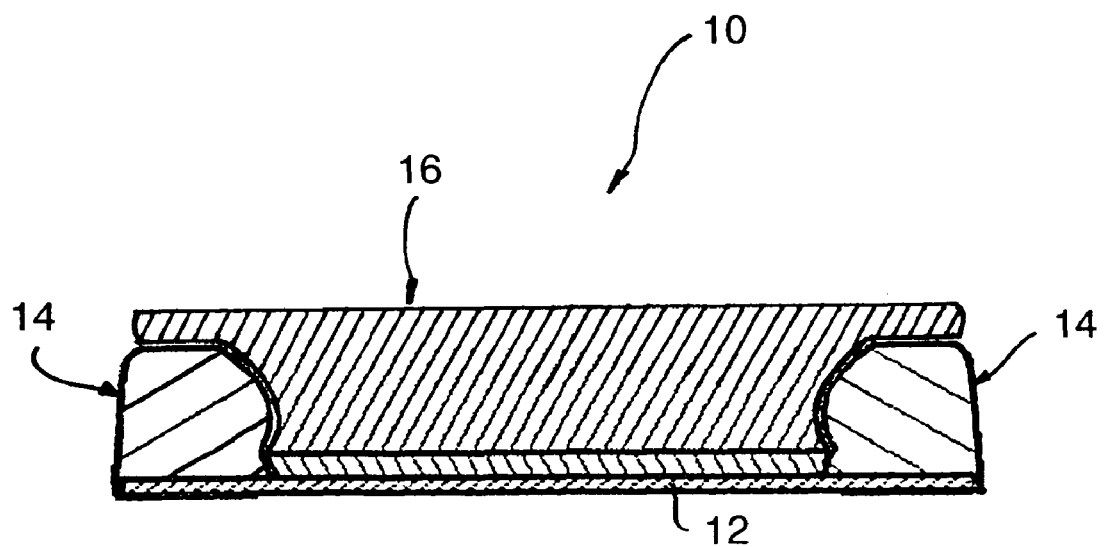
FIG. 6 shows a cross-sectional view, corresponding to FIG. 2, through a modified embodiment of the upholstery element according to the invention.

In a modified embodiment illustrated in FIG. 6, the upholstery part 16 has a T-shaped cross section, the T-foot of which lies between the side parts 14 and the T-crosspieces of which cover the side parts 14, so that, as seen in a top view, the upholstery element 10 has a closed surface. This solution has hygienic benefits, since body fluids and other fluids or impurities cannot penetrate into the gaps between the side parts 14 and the upholstery part 16.

The upholstery part 16 is held securely on the upholstery element 16 without straps, touch-and-close connections or the like which cannot easily be cleaned.

Although a preferred exemplary embodiment is shown and described in detail in the drawings and in the above description, this is to be considered as purely illustrative and not as restrictive of the invention. It is pointed out that only the preferred exemplary embodiment is illustrated and described, and all variations and modifications which come in the present time and in future within the scope of protection of the invention are to be protected.

While the present invention has been illustrated and described with respect to a particular embodiment thereof, it should be appreciated by those of ordinary skill in the art that various modifications to this invention may be made without departing from the spirit and scope of the present invention.

The invention claimed is:

1. An upholstery element for a patient bed, comprising:
a baseplate;
two elongate side parts formed at least partially of dimensionally stable foam which are arranged along two mutually opposite edges of the baseplate, each side part having a sloped face extending from the baseplate to an upper face of the side part and opposing the other side part; and
an upholstery part formed at least partially of soft foam and having a T-shaped cross section, the T-shaped cross section including a foot and a crosspiece, the foot fitting between the elongate side parts such that each side of the foot bears at least partially against the sloped face of the respectively adjacent side part, and such that the crosspiece at least partially covers upper surfaces of the side parts,
at least one projecting portion being formed and arranged at least on one of the sloped faces of the side parts such that the at least one projecting portion removably engages into an associated recess on the foot of the upholstery part when the upholstery part is arranged between the side parts, wherein the upholstery part is vertically removable from the side parts without moving the side parts on the baseplate.

2. The upholstery element according to claim 1, in which the side parts comprise integral foam.

3. The upholstery element according to claim 2, wherein the integral foam side parts have non-porous outer skins.

4. The upholstery element according to claim 1, in which the projecting portions are formed by convex bosses.

5. The upholstery element according to claim 4, wherein the projecting portions are part-spherical bosses.

6. The upholstery element according to claim 1, in which the upholstery part is surrounded by a water-impermeable sheath.

7. The upholstery element according to claim 6, wherein at least the outer surface of the sheath is electrically conductive.

8. The upholstery element according to claim 1, in which the upholstery part comprises a lower layer of ethylene-propylene-terpolymer foam and an upper layer of soft foam.

9. The upholstery element according to claim 8, wherein the lower layer of the upholstery part is disposed between the baseplate and the projecting portion so as to enhance the engagement of the upholstery part with the side part carrying the projecting portion.

10. The upholstery element according to claim 1, in which the baseplate comprises a material permeable to X rays.

11. The upholstery element according to claim 10, wherein the baseplate is formed at least partially of plactic.

12. The upholstery element according to claim 1, which is suitable for being arranged on a segment of a bed of an operating table which is connected in an articulated manner to a further segment of the bed.

13. The upholstery element according to claim 12, in which a shaped portion is formed on at least one longitudinal end of at least one of the side parts, such that the shaped portion at least partially covers a joint between the segments of the bed.

14. The upholstery element according to claim 1, wherein the crosspiece substantially covers the upper surfaces of the side parts.

15. An operating table with a bed which comprises a plurality of segments adjustable in relation to one another, wherein an upholstery element according to claim 1 is arranged on at least one of the segments.

* * * * *